US011064992B2

(12) United States Patent
Foerster

(10) Patent No.: US 11,064,992 B2
(45) Date of Patent: Jul. 20, 2021

(54) TISSUE REPAIR ASSEMBLY

(71) Applicant: ArthroCare Corporation, Austin, TX (US)

(72) Inventor: Seth A. Foerster, San Clemente, CA (US)

(73) Assignee: ArthroCare Corporation, Austin, TX (US)

( * ) Notice: Subject to any disclaimer, the term of this patent is extended or adjusted under 35 U.S.C. 154(b) by 244 days.

(21) Appl. No.: 16/220,737

(22) Filed: Dec. 14, 2018

(65) Prior Publication Data

US 2019/0117212 A1  Apr. 25, 2019

Related U.S. Application Data

(62) Division of application No. 14/205,498, filed on Mar. 12, 2014, now Pat. No. 10,182,806.

(60) Provisional application No. 61/776,957, filed on Mar. 12, 2013.

(51) Int. Cl.
*A61B 17/04* (2006.01)

(52) U.S. Cl.
CPC .. *A61B 17/0401* (2013.01); *A61B 2017/0403* (2013.01)

(58) Field of Classification Search
CPC ........ A61B 17/0401; A61B 2017/0403; A61B 2017/0404; A61B 2017/0406; A61B 2017/0409; A61B 2017/0411; A61B 2017/0412; A61B 2017/0414; A61B 2017/0416; A61B 2017/0417; A61B 2017/0419; A61B 2017/042; A61B 2017/0422; A61B 2017/0424; A61B 2017/0427; A61B 2017/0429; A61B 2017/043; A61B 2017/0433; A61B 2017/0435; A61B 2017/0437; A61B 2017/0438; A61B 2017/044; A61B 2017/0441; A61B 2017/0445; A61B 2017/0448; A61B 2017/045; A61B 2017/0451; A61B 2017/0453; A61B 2017/0454; A61B 2017/0458; A61B 2017/0459; A61B 2017/0461; A61B 2017/0462; A61B 2017/0464
USPC ......................................................... 606/232
See application file for complete search history.

(56) References Cited

U.S. PATENT DOCUMENTS

2013/0123810 A1* 5/2013 Brown ............... A61B 17/0401
606/144

* cited by examiner

*Primary Examiner* — Wade Miles
*Assistant Examiner* — Kankindi Rwego
(74) *Attorney, Agent, or Firm* — Norman F. Hainer, Jr.

(57) ABSTRACT

The present disclosure includes a soft material anchoring system including an elongate, tubular braided soft anchoring implant. The implant has a first elongate state where the implant may easily slide within a bone tunnel, and a second axially compressed state where the implant is wedged within the bone tunnel. The implant also includes at least one suture pathway that extends along and through an implant side wall; this pathway receives at least a portion of a length of suture that is also attached to soft tissue. This length of suture may slide along the suture pathway and transition the implant from the first elongate state to the second compressed state. The system also includes a binding element that at least partially extends within the implant, the binding element having both a first larger binding portion and a second smaller sliding portion.

18 Claims, 8 Drawing Sheets

TISSUE REPAIR ASSEMBLY

CROSS-REFERENCE TO RELATED APPLICATIONS

This application claims priority to U.S. application Ser. No. 14/205,498, filed Mar. 12, 2014, which claims priority to U.S. provisional application No. 61/776,957, filed Mar. 12, 2013, entitled "Tissue Repair Assembly". This application also incorporates by reference a commonly assigned application, filed Nov. 14, 2012, U.S. application Ser. No. 13/677,112, US publication No. 2013/0123810 the complete disclosure of which is hereby incorporated by reference in its entirety for all purposes.

FIELD OF THE INVENTION

This invention relates generally to methods and apparatus for attaching soft tissue to bone, and more particularly to anchors and methods for securing connective tissue, such as ligaments or tendons, to bone. The invention has particular application to arthroscopic surgical techniques for reattaching the rotator cuff to the humeral head, in order to repair the rotator cuff.

BACKGROUND

There is an ever-increasing demand for more minimally invasive surgical techniques. The lower morbidity seen in endoscopic and arthroscopic surgery makes them very appealing to both patients and physicians. These technologically-advanced procedures include many forms of soft tissue to soft tissue repairs and soft tissue to bone repair. Examples of these procedures in orthopedic surgery include rotator cuff repair, labral repair, biceps tenodesis, and anterior cruciate ligament reconstruction. Other examples in other surgical subspecialties include, but are not limited to, hernia repair, hysterectomies, and laparoscopic gastric bypass.

Many orthopedic surgery procedures involve the use of anchoring devices that attach soft tissue to bone. Most of these procedures and techniques rely on the use of polymers, metal, or biodegradable compounds. The use of these materials often requires relatively large holes placed in bone. If these devices ever loosen, one is faced with the issue of having a potentially hard device in a joint, which can cause degradation of the joint and/or place the patient at risk for developing arthritis. Certain polymeric devices, such as those made with polylactic acid (PLA), can weaken bone, predisposing the patient to fracture. Finally, metal devices can cause scatter on MRI, making follow-up images inaccurate.

In addition, two major challenges facing all surgeons and endoscopic surgeons in particular, are knot tying and suture management. Use of multiple sutures may lengthen procedure time, producing higher risk to the patient and lower repair predictability. Endoscopic knot tying is also very challenging. For example, arthroscopic soft tissue biceps tenodesis requires multiple passes of suture through the tendon and rotator cuff, followed by retrieval and knot tying which require a great deal of skill.

Solutions have been developed as an alternative to complex suture management, particularly for soft tissue to bone fixation. For example, a device that uses predominantly soft, flexible materials in repairs has a number of key advantages: 1) The use of a less invasive techniques for implantation because the use of a material that is less brittle allows the use of smaller holes in bone; 2) The ease of MRI use in follow-up; 3) No risk of a hard device lodging in a joint or body cavity; 4) Potentially better tissue incorporation; 5) Ultimately stronger bone and lower risk of fracture.

Prior solutions for suture anchors using a flexible or suture material have come under criticism for not being stiff enough in their attachment or secure enough without tying a suture knot to fully secure the soft tissue attachment. For example, U.S. application Ser. No. 13/677,112, US publication No. 2013/0123810, the complete disclosure of which is hereby incorporated by reference in its entirety for all purposes and is commonly assigned with the current disclosure. A loose or loosening attachment may enable the tissues to move post procedurally and possibly compromising the healing process. Additionally tying a knot to secure the attachment and prevent loosening is cumbersome during endoscopic or arthroscopic procedures.

Therefore additional solutions have been developed for a device that uses only or predominantly soft flexible materials for soft tissue to bone fixation with a number of key advantages: A device that supplies a mechanism that uses primarily soft flexible materials to provide a strong anchor within the bone and does not require the use of a tertiary knot to secure the attachment so as to prevent the device from loosening.

SUMMARY

The present disclosure presents an improved knotless anchoring system for attaching soft tissue to bone. The apparatus generally includes a bone anchor, and a length of suture for coupling both with the soft tissue and then with the bone anchor.

In one aspect a soft material anchoring system is disclosed including an elongate, tubular braided soft anchoring implant, that has a first elongate state wherein the implant may easily slide within a bone tunnel, and a second axially compressed state such that the implant is wedged within this bone tunnel. At least one suture pathway extends along and through a sidewall of the implant, this pathway intended for a portion of a length of suture, so that the length of suture may slide along this suture pathway and adjust the implant from the first elongate state to the second compressed state. The system also includes a binding element that at least partially extends within the implant, with a first larger binding portion and a second smaller sliding portion.

In another aspect a method of anchoring soft tissue to bone is described including the steps of threading a length of suture through a piece of soft tissue intended to be attached adjacent the bone tissue followed by passing at least one end of the length of suture along a first suture pathway that extends both through a portion of a braided wall of a soft anchor implant and along an elongate side of the braided wall. A least one end of the length of suture extends along the pathway in a distal direction before looping over a distal end of the implant followed by extending proximally along the implant so that the at least one end of the length of suture extends proximally from the implant proximal end. The soft anchoring implant may then be inserted into a bone hole in the bone tissue and the at least one suture end may then be pulled in a proximal direction, so that the length of suture slides and causes an increase in a diameter of the soft anchoring implant so as to anchor the implant within the bone. A binding portion of a binding element may then be wedged into the implant so as to prevent the implant diameter from changing and lock the anchor within the bone tissue.

In another aspect a knotless method of locking a bone anchoring implant in an axially compressed state is described including the steps of threading two suture ends of a length of suture along and in between an elongate wall of a soft braided material anchoring implant, so that both suture ends extend from a proximal end of the implant, followed by pulling at least one suture end proximally so as to slide the length of suture through the implant and shorten the implant axially while expanding the implant radially, to render the implant in an axially compressed state. A binding element may then be drawn into the implant, the binding element sized so as to wedge into the implant and increase pressure between the braided material and the length of suture so as to cause a frictional lock between the braided material and the length of suture and maintain the axially compressed state.

The invention, together with additional features and advantages thereof, may best be understood by reference to the following description taken in conjunction with the accompanying illustrative drawing.

BRIEF DESCRIPTION OF THE DRAWINGS

For a detailed description of exemplary embodiments, reference will now be made to the accompanying drawings in which.

NOTATION AND NOMENCLATURE

Figure 1A:
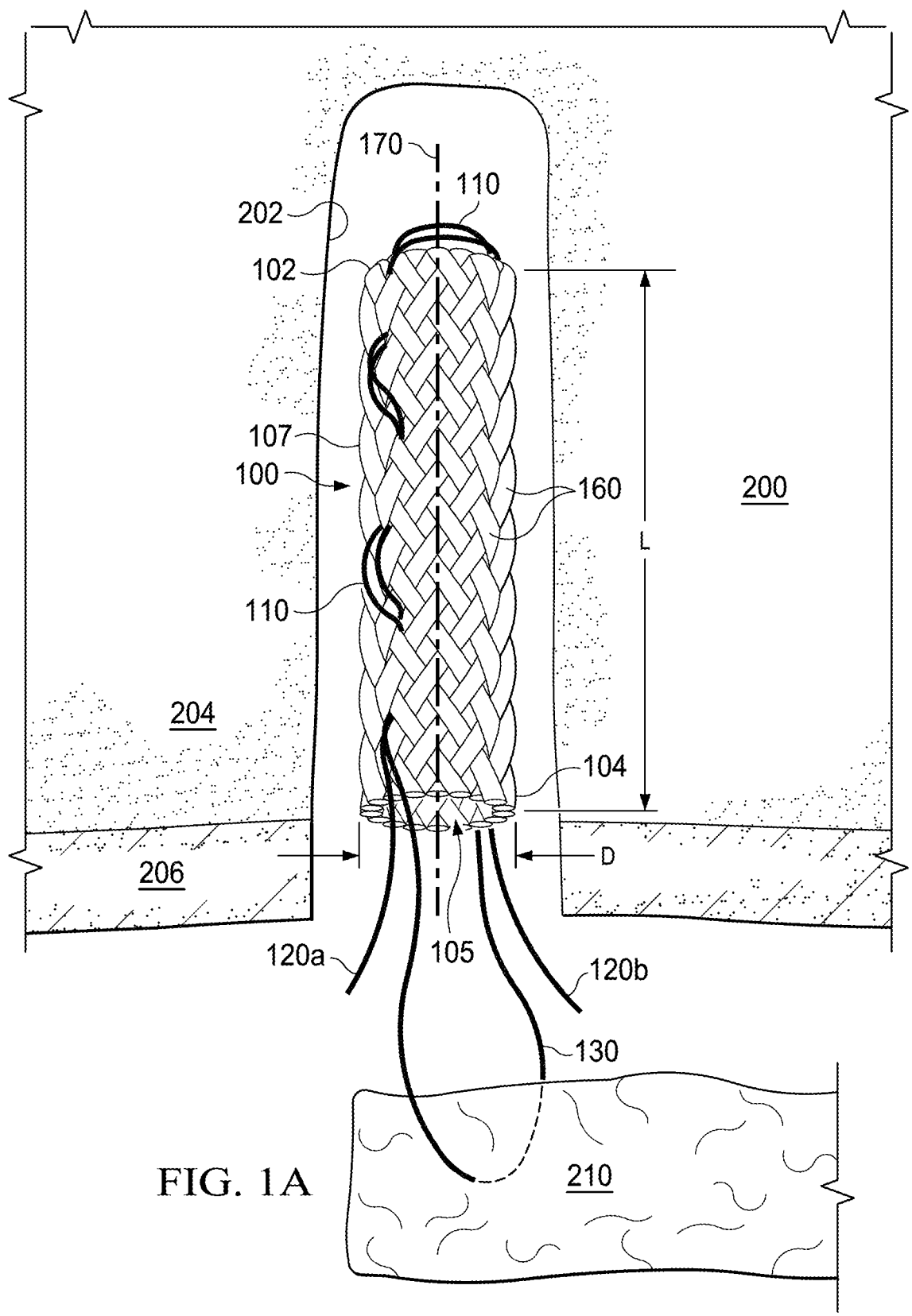
FIG. 1A is a perspective view of the soft anchoring implant in an elongated state within bone tissue, with binding element not shown for simplicity, in accordance with some embodiments.

Certain terms are used throughout the following description and claims to refer to particular system components. As one skilled in the art will appreciate, companies that design and manufacture medical devices may refer to a component by different names. This document does not intend to distinguish between components that differ in name but not function.

In the following discussion and in the claims, the terms "including" and "comprising" are used in an open-ended fashion, and thus should be interpreted to mean "including, but not limited to . . . ." Also, the term "couple" or "couples" is intended to mean either an indirect or direct connection. Thus, if a first device couples to a second device, that connection may be through a direct connection, or through an indirect connection via other devices, components, and connections. Further, the terms "proximal" and distal are intended to refer to proximity relative to a bone anchor applicator. Thus, if a first device is distal and a second device is proximal, the second device is nearer to the bone anchor applicator than the first device.

Reference to a singular item includes the possibility that there are plural of the same items present. More specifically, as used herein and in the appended claims, the singular forms "a," "an," "said" and "the" include plural references unless the context clearly dictates otherwise. It is further noted that the claims may be drafted to exclude any optional element. As such, this statement serves as antecedent basis for use of such exclusive terminology as "solely," "only" and the like in connection with the recitation of claim elements, or use of a "negative" limitation. Lastly, it is to be appreciated that unless defined otherwise, all technical and scientific terms used herein have the same meaning as commonly understood by one of ordinary skill in the art to which this invention belongs.

Where a range of values is provided, it is understood that every intervening value, between the upper and lower limit of that range and any other stated or intervening value in that stated range is encompassed within the invention. Also, it is contemplated that any optional feature of the inventive variations described may be set forth and claimed independently, or in combination with any one or more of the features described herein.

All existing subject matter mentioned herein (e.g., publications, patents, patent applications and hardware) is incorporated by reference herein in its entirety except insofar as the subject matter may conflict with that of the present invention (in which case what is present herein shall prevail). The referenced items are provided solely for their disclosure prior to the filing date of the present application. Nothing herein is to be construed as an admission that the present invention is not entitled to antedate such material by virtue of prior invention.

DETAILED DESCRIPTION

Before the various embodiments are described in detail, it is to be understood that this invention is not limited to particular variations set forth herein as various changes or modifications may be made, and equivalents may be substituted, without departing from the spirit and scope of the invention. As will be apparent to those of skill in the art upon reading this disclosure, each of the individual embodiments described and illustrated herein has discrete components and features which may be readily separated from or combined with the features of any of the other several embodiments without departing from the scope or spirit of the present invention. In addition, many modifications may be made to adapt a particular situation, material, composition of matter, process, process act(s) or step(s) to the objective(s), spirit or scope of the present invention. All such modifications are intended to be within the scope of the claims made herein.

The technology disclosed herein would have a broad application in orthopedic surgery for an animal, such as a human. This includes repairs of tendons to bone, bone to bone, tendons to tendons, and ligaments to bone, including ligament reconstruction. Some of these procedures include, but are not limited to, labral repairs in the shoulder and hip, capsular plication, biceps tenodesis, anterior cruciate ligament reconstructions, rotator cuff repairs, meniscal repair, triangular fibrocartilage (TFCC) repairs, and ankle stabilizations. There can also be an application for fracture repair, such as for repairing small butterfly fragments in long bone fractures. Applications outside of orthopedic surgery include: cardiac surgery (where pledgets are used in the implantation of prosthetic heart valves), general surgery (for hernia repair, nissen fundoplication, and parenchymal compression), plastic surgery (for tissue to tissue repair), Ob-Gyn (for cuff closure in laparoscopic hysterectomy and bladder support).

Figure 1B:
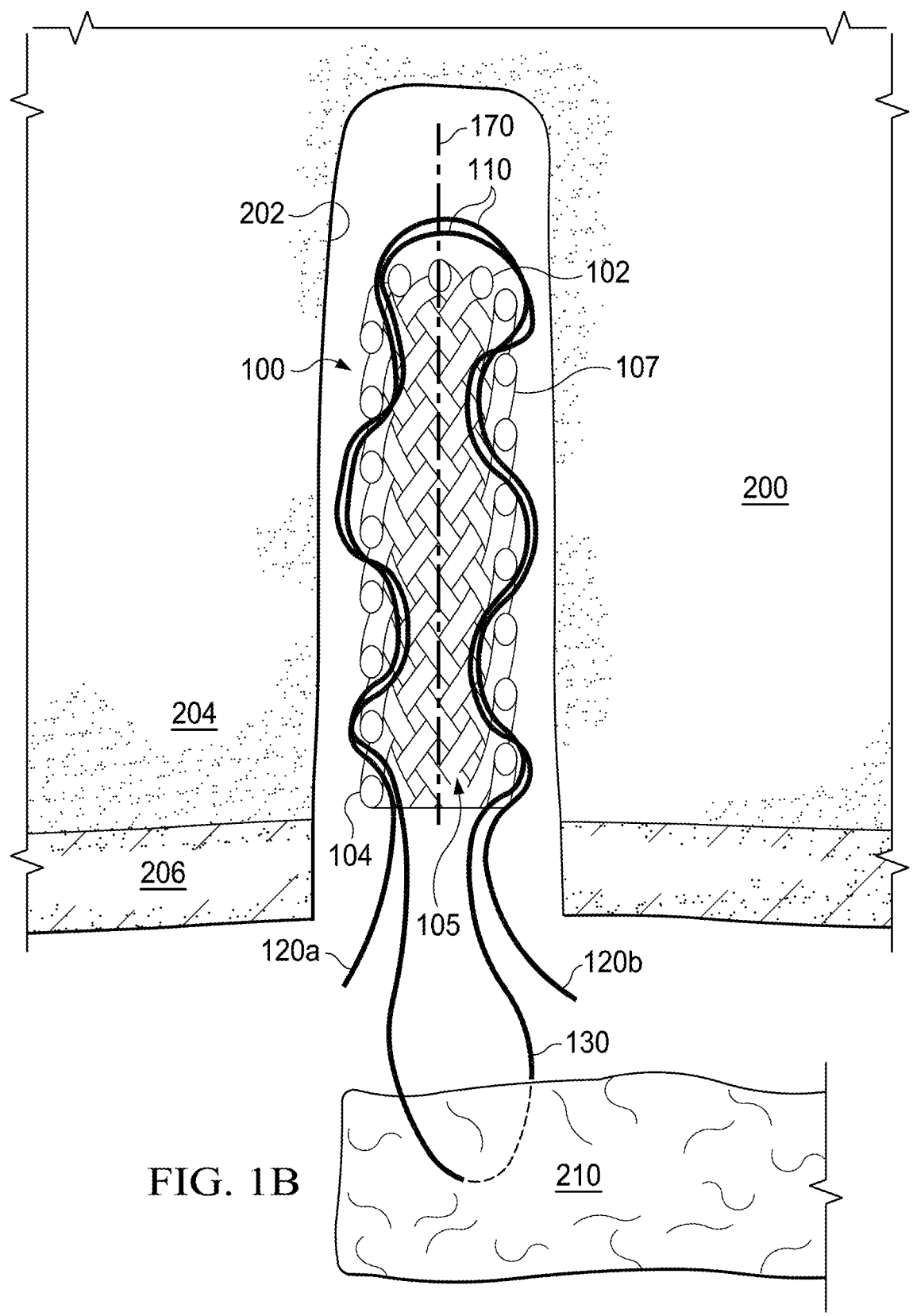
FIG. 1B is a cross sectional view of the soft anchoring implant in an elongated state, as shown in FIG. 1A, with binding element not shown for simplicity, in accordance with some embodiments.

FIGS. 1A and 1B show an embodiment of a soft anchoring implant 100 already inserted into a bone tunnel 202, disposed within bone tissue 200. Bone tunnel 202 may be prepared ahead of time using a separate tool or instrument or alternatively the space may be created by an implant insertion instrument (not described here) simultaneously while inserting the implant within the bone. Bone tissue includes both soft cancellous bone tissue 204 and a cortical bone layer 206. It is preferable for the soft anchoring implant 100 to be inserted so that the anchoring implant proximal end 104 is disposed approximately adjacent to or slightly distal of the cortical layer 206. A binding element is not shown in this figure for simplicity and will be described in later figures. When used as part of a tissue repair system, the implant 100 is generally intended to anchor and lock a length of suture within bone or other hard tissue and allow for the attachment of soft tissue as in an orthopedic repair. In certain embodiments, the soft anchoring implant 100 may be loaded into a delivery system, such as a system described in the commonly assigned application, Ser. No. 13/677,112, and deployed into hard tissue such as bone to facilitate a repair or deployed as a retaining anchor for two pieces of soft tissue. In other embodiments, the tissue repair system may be utilized as described herein to facilitate the attachment of synthetic tissue or materials to other structures within the body. In further embodiments multiple implants 100 may be loaded within a delivery system and placed adjacent to each other, with an interconnecting length of suture to attach a longer piece of soft tissue to bone.

Generally described, the soft anchoring implant 100 is a three-dimensional, tubular shape which may have one open proximal end 104 and one closed distal end 102, with a lumen 105 that is changeable in shape and an outer wall 107; the lumen 105 and outer wall 107 defining a sidewall or thickness. In this elongate state, the implant 100 may typically be sized in the range of 10 mm-30 mm in length with a width or diameter of 1 mm-5 mm. Anchoring implant 100 is shown in FIGS. 1A and 1B in a first, pre-deployed state in which braided fibers 160 are in an elongated state. The braided fibers 160 of the implant 100 are more aligned in an orientation parallel to longitudinal axis 170 and are generally more compacted. Axis 170 is generally aligned with the insertion direction of the implant within bone, or aligned with the bone tunnel longitudinal axis and does not alter in orientation when in a secondary deployed state. Soft anchoring implant 100 may be pulled and manually manipulated to achieve this elongate configuration or the use of specialized manufacturing fixtures may be employed, such as a funnel or a tube, which may compel the implant 100 to achieve this first elongate configuration to better fit within an inserter tube, such as a tube described in the commonly assigned application Ser. No. 13/677,112. The embodiment shown in FIGS. 1A and 1B may be formed from a coarse braided material. More specifically, the structure utilized may be a cylindrical, helically wound braid, such as the common biaxial braid. Pulling the entire braid along its length (i.e., putting the braid in tension) lengthens and narrows it. The length (L) is gained by reducing the angle between the braided fibers 160 of the wound braid at the crossing points of the braided fibers 160 so that the braided threads 160 align mostly parallel, which also reduces the radial distance between opposing sides and hence the overall circumference. When counter traction occurs, the opposite action occurs, and the braid contracts axially and expands radially, in this case by increasing the angle between the braided threads 160. This helically wound braid provides an advantage in that the structure can collapse and elongate without altering the longitudinal axis of the implant, naturally due to the alignment of the braids.

FIGS. 1A and 1B also show operative suture length 110 that, prior to inserting the anchoring implant 100 into the bone tunnel, may be threaded through soft tissue 210, and then, using a snare (not described here) threaded through anchoring implant 100. After threading the suture length 110 through the soft tissue 210, a first and a second suture tail 120a and 120b result, which may then both be passed or pulled through a portion of the side wall or thickness of the implant 100 in a generally distal direction. At least one suture tail 120a or 120b may be pulled through from an origination side that is either the exterior side 107 or the lumen side 105. It is preferable that the suture tails 120a, b extend between braids 160 and they may or may not pass through the entire side wall before extending a short distance along the anchor sidewall and then snaking or returning through a portion of the sidewall to the origination side of the implant 100 for a short distance again. At least one of the suture tails 120a, b may then pass back into the thickness or wall of the implant 100. Although two suture tails 120a, b are shown, the inventors have contemplated a single tailed application, with a single suture tail extending from the tissue and being woven into the wall of the implant and manipulated for anchoring and tensioning (not shown). Once a suture tail 120a and/or b has reached the anchor distal end 102 it may loop across to an opposing side of the anchor 100 and return in a similar fashion extending proximally.

Shown more clearly in FIG. 1B, first suture tail 120a may pass into the implant walls at an approximate opposing side of the implant 100 relative to the second suture tail 120b. Each tail 120a and 120b is shown with a path snaking in and out of the implant wall, while traveling in a general distal direction, as far as the anchor distal end 102, where each suture tail 120 passes around the distal end 102 of the implant 100 to the approximate opposing side of the implant 100, before repeating the penetrations and exiting back out around the open, proximal end 104 of the implant 100. Again, the first tail 120a may enter and then exit the proximal end 104 at approximately opposing sides of the implant 100, and the first suture tail 120a may exit the implant 100 at approximately the opposite side of the implant 100 to the second suture tail 120b. This arrangement may allow the implant to expand radially more evenly on each side of the implant. Additionally the path taken by the first suture tail 120a as it extends distally through the implant 100 may define the return path taken by the second suture 120b and vice versa. In alternative embodiments, the suture tail 120a or 120b may take an alternative return path through the implant 100. In other alternative embodiments, the suture tails 120a and 120b may both enter at differing points that are spaced away from each other, but not necessarily on opposing sides of the implant 100. As an example two suture tails 120a and 120b may pass through implant 100 in a side-by-side fashion, or two suture tails 120a and 120b may pass through in a cross-over fashion. Having multiple suture lengths 110 may have the added benefit in the surgical procedure of being able to anchor multiple pieces of tissue independently to the bone or other tissue where the soft anchoring implant resides. Multiple sutures also allows for the use of a greater variety of suturing and repair techniques. Additionally, multiple suture strands may allow for more effective deployment of the soft anchoring implant into the bone or other hard tissue by virtue of the fact that they may inherently cause more wrinkling, folding, or puckering of the soft anchoring implant thus giving it better retention properties. In additional embodiments (not shown here), the soft anchoring implant can include three or more suture lengths associated with it. It is understood that these suture lengths may be configured in a sided-by-side fashion or in any variety of cross-over fashion. It is also understood that the suture lengths may initiate interface with the soft anchoring implant through an inside of the lumen or from the outside the lumen and may enter and exit the walls of the soft anchoring implant once or multiple times.

At least two suture path lumens or pathways are now defined by the passage of the suture tails 120a and 120b through the walls of the implant 100. The suture length 110 is not locked into place with respect to the soft anchoring implant 100, but rather it remains slideable through or along the walls of the implant 100. This slideability aspect is important to the function of the implant 100 as it relates to its ability to attach and repair tissues. As a result of threading the suture tails 120a and 120b through implant 100, a suture loop 130 is created, threaded through soft tissue 210.

Figure 2:
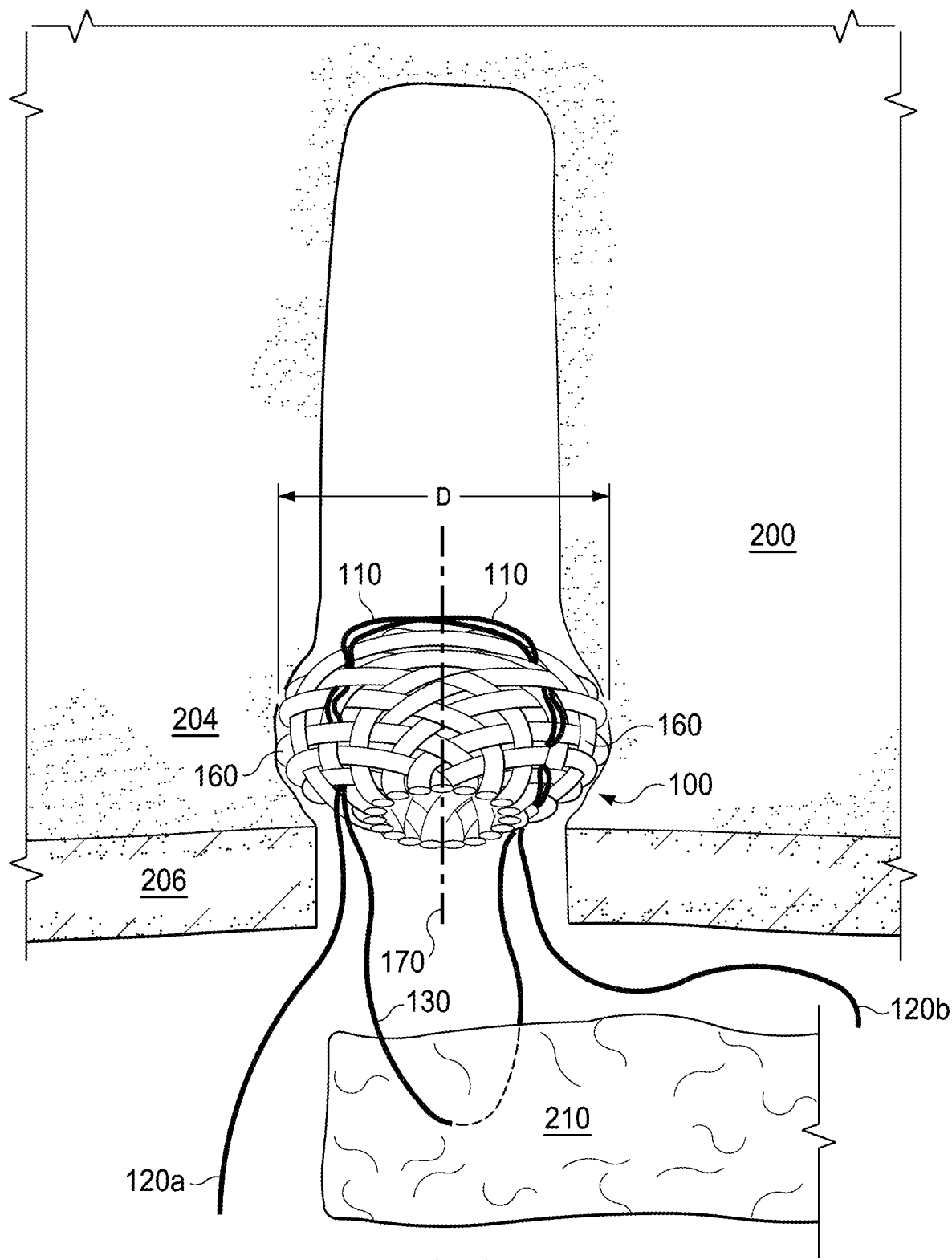
FIG. 2 is a perspective view of the soft anchoring implant in a compressed deployed state within bone tissue, with binding element not shown for simplicity, in accordance with some embodiments.

By tensioning the sutures length 110, i.e. pulling on at least one of the suture tails 120a and 120b as well as the suture loop 130, the suture length within the implant shorten and straighten and the braided fibers 160 of the textile assume an orientation more orthogonally aligned with respect to the axis 170. FIG. 2 shows this second, deployed state, wherein the implant 100 is generally shortened, to become more ball shaped and of a larger maximum diameter (D) than in the first, pre-deployed state. The inherent fiber size of textile or braided material combined with the weave or opening or tick size may impact the ability of the implant to achieve varying degrees of the pre-deployed and deployed states. A fiber or yarn size of 200 to 1500 denier is generally appropriate with a braid of 7 to 25 pics per inch (PPI). Tightly braided constructs made of small fibers, for example 100 denier at 50 PPI, would not allow the orientation change of the fibers which facilitate the contraction and expansion of the implant and thus inherently have lower retention strength. Woven constructs are similarly restricted in their expansion capability due the orientation of the fiber weave. The ratio of the implant length to diameter (or width) (D) of the soft anchoring implant 100 may play some role in achieving better retention properties. For example, a longer implant of a given diameter may better anchor itself in tissue by virtue of the fact that it would have more surface area contact with the surrounding tissue or bone. Alternatively, there may be some benefit to a soft anchoring implant 100 with a relatively large diameter (or width) in relation to the hole through which it is pushed. There are limitations to the diameter of the implant however, as imposed by the space within an insertion instrument used to deploy the implant. However, in embodiments, a soft anchoring implant 100 may fit into an inserter instrument (not described here) or other delivery mechanism with a smaller diameter. This is possible because of the soft, flexible nature of the implant, with its combination of yarn size and pic count allowing it to elongate and compress to a substantially smaller diameter to allow for placement into an inserter tube (not described here) without necessarily folding over on itself.

FIG. 2 shows the suture ends or tails 120a, b and the suture loop 130 having been pulled proximally, to distort the loose braided suture implant anchor 100 inside the bone tunnel. Pulling on the suture tails 120a, b creates two fairly straight suture lumens or pathways within the wall of the anchor implant 100, the suture pathways defined by the path of the length of suture 110 through the braided anchoring implant 100. Again, for simplicity a binding element is not shown in FIG. 2, but will be described later. The soft anchoring implant 100 may preferably push into the more malleable cancellous bone tissue 204 so as to form this deployed state embedded within the cancellous bone, while the cortical bone 206 will remain unchanged, so that the anchor is now naturally contained within the bone 200. In some physiologies however, the cancellous bone tissue 204 may be substantially the same hardness as the cortical bone 206. In these physiologies, the rough nature of the boney hole 202 provides enough friction with implant 100 to retain implant 100 while soft tissue 210 is tensioned.

Figure 3:
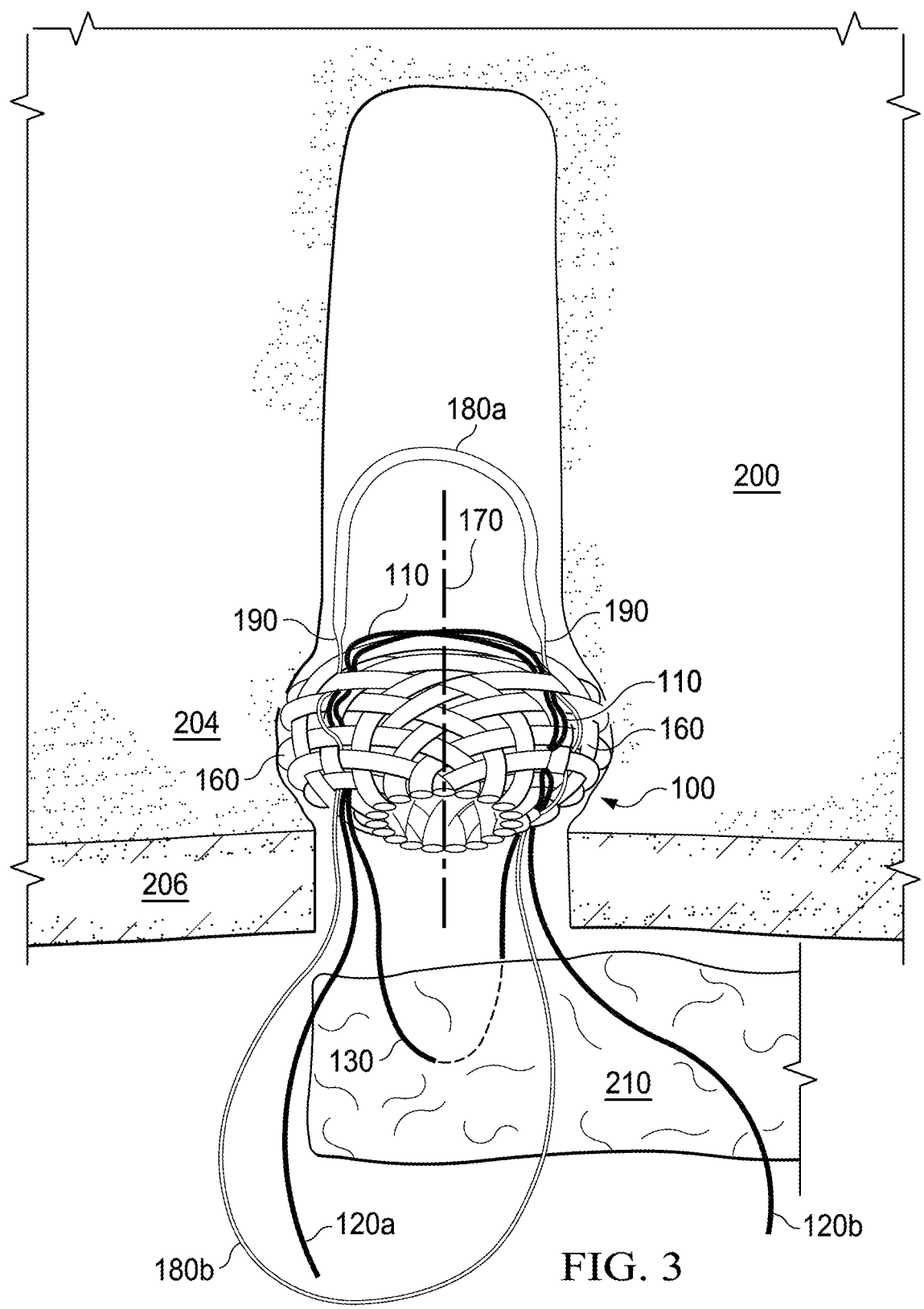
FIG. 3 is a perspective view of the soft anchoring implant in a compressed state, showing soft tissue apposed with bone tissue, in accordance with some embodiments.
Figure 4:
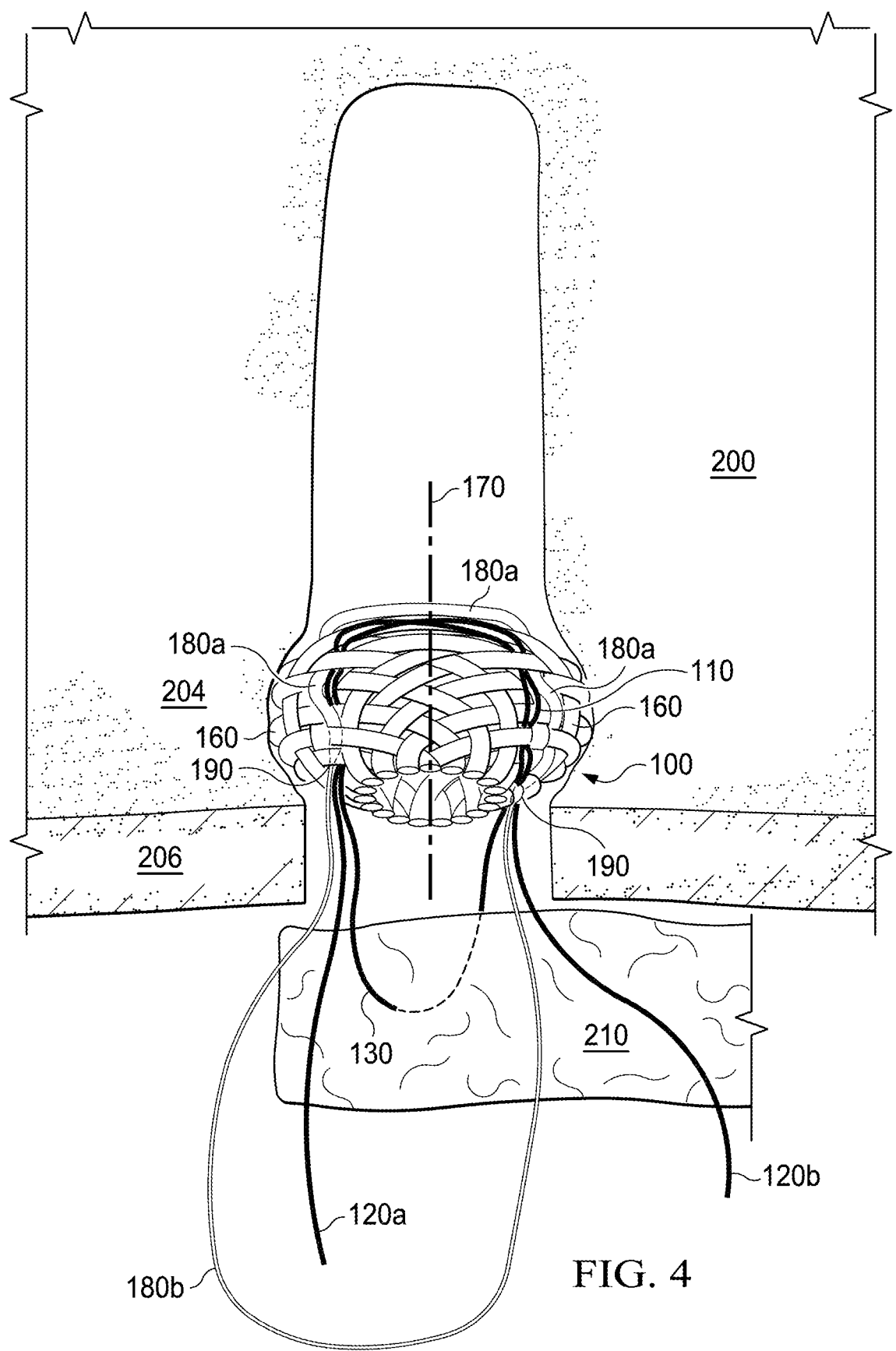
FIG. 4 is a perspective view of the soft anchoring implant in a compressed state with binding element deployed, in accordance with some embodiments.

In FIG. 3 the soft tissue 210 is shown positioned adjacent with bone 200 and more particularly to the cortical bone 206. This is achieved by pulling on at least one suture tail 120a or 120b so that the length of suture 110 slides through at least one pathway and pulls the suture loop 130 closer to the bone tissue 200. Binding element loop with distal portion 180a and proximal portion 180b are shown in FIGS. 3 and 4, with a distal portion 180a that may be relatively large in diameter or width compared with the length of suture 110 and also may be relative large in size compared with the diameter or width of the binding element proximal portion 180b. Binding element 180a, b may preferably also made from a flexible biocompatible materials and may simply be variants of the material used for the implant anchor 100 and/or length of suture 110. In some embodiments however, binding element 180a, b is preferably a biocompatible material that has a higher tensile strength than traditional suture such as stainless steel so that it does not distort or extend upon the application of tension, for improved positional accuracy, as will be described later. Binding element distal end 180a is shown as a loop, but may alternatively be two binding element tails with knotted ends or thicker ends or wedges. Binding element distal portion 180a may also be defined by several looped suture segments that are intertwined with binding element proximal portion 180b. Binding element 180a and 180b is shown extending proximally and distally through the wall or thickness of the implant 100, possibly following the same pathway of at least a portion of the length of suture 110 through and along the implant 100. Binding element distal end 180a may be relatively thicker or larger in diameter than the proximal end 180b with a tapered transition 190 therebetween. Tapered transition 190 is shown in FIG. 3, distal to the implant distal end 102. It is preferable to have the relatively thinner or smaller diameter portion of binding element 180 within pathways along the implant 100, while the length of suture 110 is threaded and slid, as described in FIGS. 2 and 3, so as to minimize any restriction to the slideability of the suture length 110.

FIG. 4 shows the soft anchoring implant 100 with the soft tissue 210 secured directly adjacent to the bone tissue 200 via the suture loop 130, and with the thicker distal portion of binding element 180a drawn into the anchoring implant. Inserting the thicker portion of the binding element 180a into the implant locks the implant 100 into the secondary state and also inhibits the length of suture 110 from sliding. By wedging the distal thicker portion of the binding element 180*a* within the implant, the soft materials, including the braided fibers 160 and length of suture 110 are now compressed against each other and though this pressure and friction, are now restricted from sliding relative to each other. Hence the length of suture 100 may now be hindered from sliding though the implant 100 and the braided fibers 160 may no longer slide over each other to change shape; the implant 100 is anchored and the soft tissue is fixed onto the bone without the need of tying a knot. Shown here, the binding element distal portion 180*a* is drawn into the implant so as to be disposed along at least one lumen or pathway defined by a portion of the length of the suture 110. In alternative embodiments, the binding element may be drawn into an alternative pathway through and along the anchoring implant 100.

Being drawn so that the binding element distal portion 180*a*, length of suture 110 and braided fibers 160 are all in contact may be preferable, as it may improve and localize the frictional resistance directly between the length of sutures 110, braided fibers 160 and binding element distal portion 180*a*. A portion of binding element distal portion 180*a* may be in contact with both the implant braids 160 and the portion of the length of suture 110 disposed within the suture pathway. Binding element distal portion 180*a* may be positioned by pulling the proximal portion 180*b* in a generally proximal direction, which may put significant tension on the binding element 180 with the potential for stretching and thinning of the binding element distal portion 180*a*. This may affect the ability for the distal portion 180*a* to adequately lock the anchor 100 as well as make positioning of the binding portion 180*a* less accurate or reliable.

Therefore, binding element 180 may preferably be a flexible loop or length, but also operable to withstand this higher tensile load, and may be manufactured from a material other than suture such as alternative polymers or stainless steel. The binding element distal portion 180*a* is sized so as to be relatively easily drawn or wedged into the implant, and must also be sized so as to adequately move the braided fibers 160 and length of suture 110 towards each other (reduce the gaps) and frictionally lock the implant 100. A tapered transition 190 between the binding element proximal portion 180*b* and distal portion 180*a* may adjust for this sizing requirement, which may alter depending on the bone tunnel sizing and bone material properties and variations in the manufacturing process for example. Shown in FIG. 4, the tapered transition 190 is drawn proximally all the way adjacent the proximal portion of the implant 100. This position may alter, depending on the reasons given above. The binding element distal portion 180*a* acts so as to permanently lock the implant 100 in the second state form and prevent the length of suture from moving without the need of tying knots. Once the distal portion 180*a* is wedged, the length of suture 110 may not slide, and the braids may not slide over each other, so implant 100 is fixed in the second compressed, deployed or anchoring state, so that it may not exit the bone tunnel.

In an alternative embodiment, binding element distal portion 180*a* may slide into an alternative pathway snaking in and out of and along the wall of the implant 100 (not shown here), and not the same pathway as the length of suture 110. This may also increase the internal pressure on the implant 100 and essentially tighten the braided structure, so as to force more contact and hence more friction between the implant braids 160 and length of suture 110, reducing the ability of the length of suture 110 to slide. The braided structure of the implant 100 will also have less ability of slide over itself, helping to maintaining the anchor implant 100 in the second, anchoring state, without the need for a suture knot.

Figure 5:
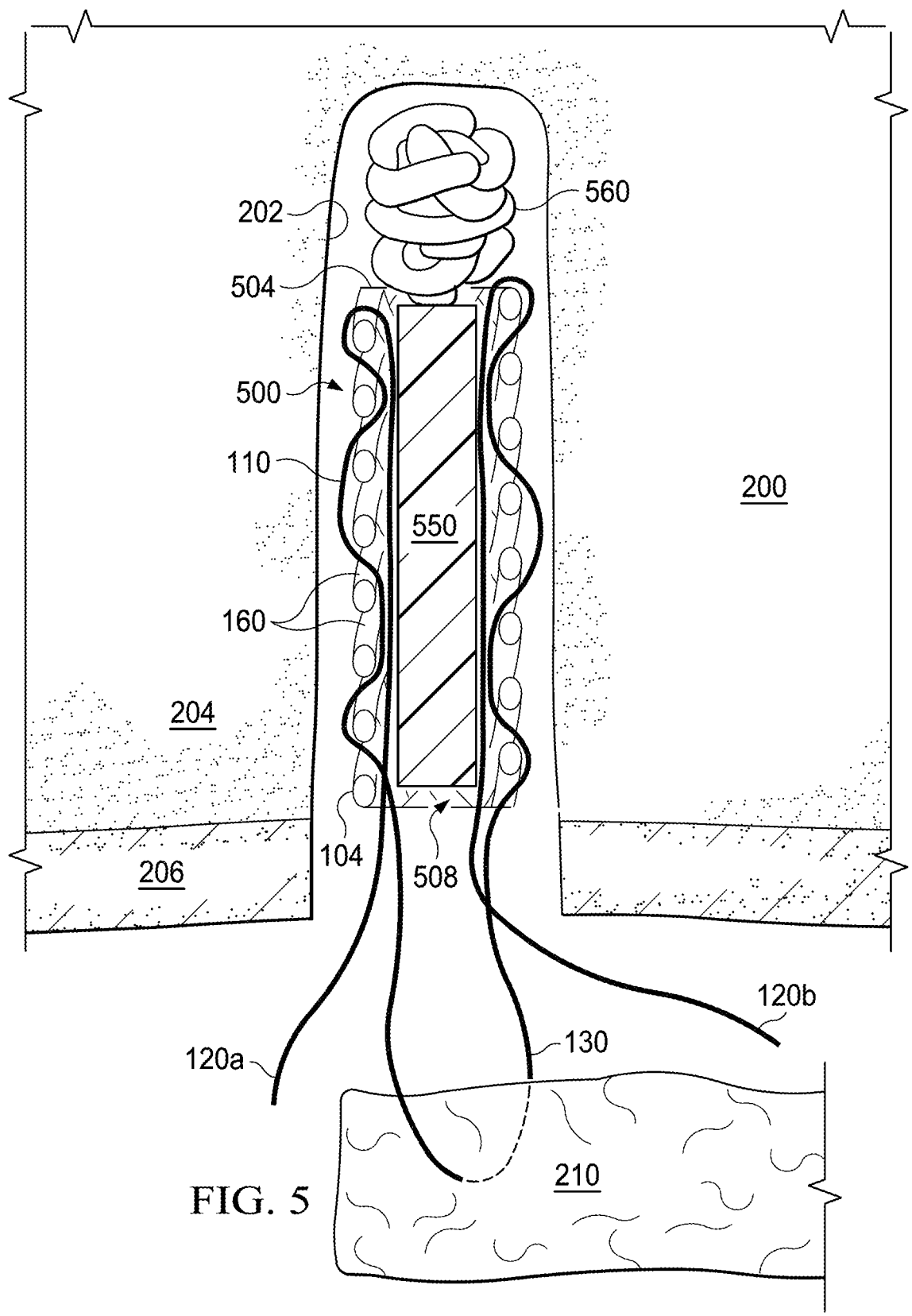
FIG. 5 is a cross sectional view of an alternative embodiment of a soft anchoring implant in an elongated state with a soft knotted plug.

FIG. 5 shows an alternative embodiment of a binding element including a flexible material knotted anchor plug 560 for a soft anchor implant 500. Similar to previously described embodiments, suture length 110 is shown looped through soft tissue 210 and threaded though implant 500. In this embodiment it may be preferable for the return path of suture length 110 and suture tails 120*a* and 120*b* to extend along an internal lumen 508 of implant 500 rather than continuing to weave in and out through the thickness of anchoring implant 500. Anchoring implant 500 is also shown with an open distal end 504, to allow knotted plug 560 to slide into position once the soft tissue has been correctly positioned. Knotted plug 560 is made from a soft, flexible material, similar to materials described previously and includes a series of tightly tied knots directly adjacent to each other so as to create an elongate structure of a certain diameter similar or larger to a diameter of lumen 508. Not shown here, but similar to previous embodiments of anchoring implants, the length of suture 110 and loop 130 may be pulled to adjust the implant 500 to form a second compressed state and the suture tails 120*a* and 120*b* may then be pulled proximally to slide the length of the suture 110 though implant 500, so as to correctly place the soft tissue 210 up against the bone tissue 200. A spacer or "dummy" plug 550 may be disposed within lumen 508 during these steps, and act as a placeholder while adjusting the length of suture 110. Spacer plug 550 may be of any material, and not necessarily a flexible implantable material, but should be a material that may easily slide within lumen 508. Spacer plug 550 may have elongate grooves for the length of suture to lie in as it extends along the lumen 508 so as to allow the length of suture 110 to easily slide. Spacer plug 550 is connected or coupled with the proximal end of knotted plug 560 and may be tapered with a maximum diameter that is approximately equivalent to or slightly smaller than knotted plug 560.

Once the soft tissue 210 is in the correct position, the spacer plug 550 may be pulled proximally so as to wedge the knotted plug 560 within lumen 508. Knotted plug 560 is sized so as to wedge within lumen 508 to increase the pressure on the braided fibers 160 of implant 500 and wedge the implant 500 within the bone tunnel. Knotted plug 560 is also sized to as to increase the friction between the length of suture 110 and fibers 160 within implant 100, so as prevent the length of suture 110 from sliding anymore and hence keeping the soft tissue 210 in the correct position. Spacer plug 550 may be made from a soft material, or may alternatively be a stainless steel tube or cable with a breakaway eyelet or aperture connecting the plug 550 with the plug 560 (not shown in figure). A stainless steel material or high tensile strength material may more accurately position the plug 560 within the implant 500 than a softer material or suture material. Similar to previous embodiments, the significant tensile loading on the spacer plug 550 as it is withdrawn to insert the plug 560 within the implant may potentially deform or stretch a spacer plug 550 made from a softer material, affecting the positional accuracy of the knotted plug 560. Spacer plug 550 may preferably be disconnected from knotted plug 560 once the knotted plug 560 is wedged within lumen 508. Alternative embodiments for the knotted plug 560 have been contemplated by the inventors including an enlarged suture structure that is not enlarged using knots as in knotted plug 560. Such enlarged suture structures may contain one or multiple eyelets through which multiple strands of suture reside. Multiple strands may be either looped or segmented and it is these multiple strands that act similarly to the knotted plug 560. Said eyelets may be woven or simply formed by the crossing weaves in a braided structure of a common braided suture. This alternative embodiment may be preferable as it would fall apart easily if the anchor inadvertently became detached from the bone so as to be loose in the joint; loose suture structures within the joint tend to cause less damage to the joint than harder structures.

Figure 6:
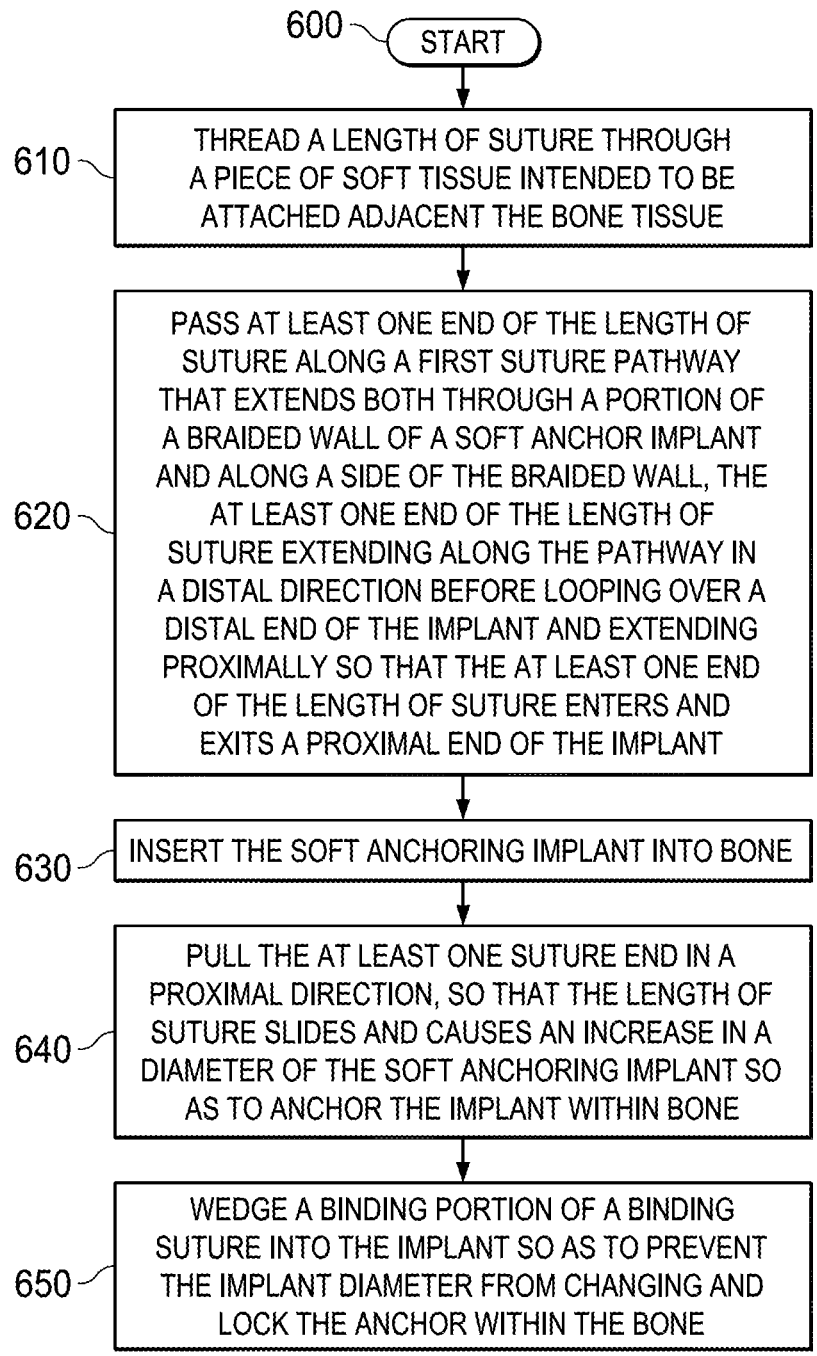
FIG. 6 shows a flow diagram of a medical procedure, including anchoring tissue to bone using a system according to at least certain embodiments.

Referring now to FIG. 6, a method (600) of anchoring soft tissue to bone tissue in accordance with at least some of the embodiments described herein is illustrated, including the steps of: threading a length of suture through a piece of soft tissue intended to be attached adjacent to the bone tissue (610); followed by passing at least one end of the length of suture along a first suture pathway that extends both through a portion of a braided wall of a soft anchor implant and along a side of the braided wall, (620) the at least one end of the length of suture extending along the pathway in a distal direction before looping over a distal end of the implant and extending proximally so that the at least one end of the length of suture enters and exits a proximal end of the implant. In alternative embodiments the suture pathway may not extend all the way to the distal end before returning and exiting at the proximal end of the implant. The soft anchoring implant may then be inserted into bone (630) before pulling the at least one suture end in a proximal direction, so that the length of suture slides through the implant and causes an increase in a diameter of the soft anchoring implant so as to anchor the implant within bone (640). In some embodiments the implant may be inserted into a prepared bone tunnel. In some alternative embodiments the implant may be attached to an insertion instrument (not described here) that may create the space in the bone as the implant is inserted. A binding portion of a binding element may then be wedged into the implant so as to prevent the implant diameter from changing and lock the anchor within the bone without the need of tying a knot (650). In some embodiments the step of extending proximally comprises threading the at least one end of the length of suture along a second pathway that extends both though a portion of the braided wall of the implant and along a side of the braided wall. In some embodiments the binding element has a first portion that is smaller in size than the second portion and the first portion may be disposed within the implant during the steps of threading and pulling, the first portion extending proximally from the implant, so that the step of wedging comprises pulling on the proximal portion of the binding element in a proximal direction so as to replace the first portion of the binding element with the second portion. In certain embodiments, the binding element may also partially extend along at least a portion of the suture pathways and the step of wedging places the binding element both in contact with the length of suture and the braided wall so as to wedge the suture and braids together and inhibit their relative movement. In some embodiments the first portion is a tube that is disconnected from the binding portion after the step of wedging. In certain embodiments, the step of pulling also draws the soft tissue closer to the implant and the bone tissue. In other embodiments, the implant may be part of a series of at least two soft braided implant anchors with a length of suture extending between them, that combine to re-attach a piece of soft tissue to bone.

Figure 7:
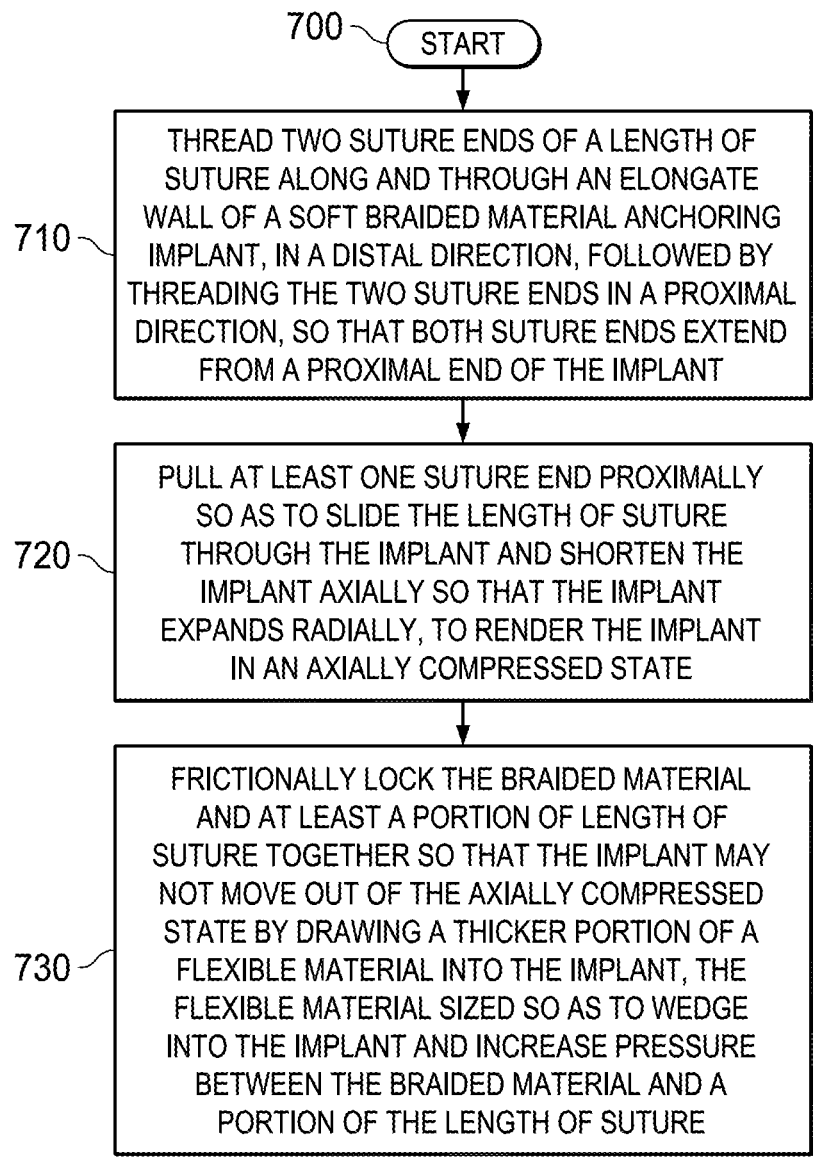
FIG. 7 shows a flow diagram of a medical procedure, using a knotless soft anchoring implant system according to at least certain embodiments.

Referring now to FIG. 7, a method (700) of knotlessly locking a bone anchoring implant in an axially compressed state in accordance with at least some of the embodiments described herein is illustrated, including the steps of: threading two suture ends of a length of suture along and through an elongate wall of a soft braided material anchoring implant, in a distal direction, followed by threading the two suture ends in a proximal direction, so that both suture ends extend from a proximal end of the implant (710), followed by pulling at least one suture end proximally so as to slide the length of suture through the implant and shorten the implant axially so that the implant expands radially, to render the implant in an axially compressed state (720). Pulling on the at least one suture end acts so as to straighten the suture and does not necessarily alter the orientation of the longitudinal axis of the implant lumen, which remains relatively unaltered during this pulling step. A thicker portion of a binding element may then be drawn into the implant, the flexible material sized so as to wedge into the implant and increase pressure between the braided material and the length of suture so as to cause a frictional lock between the braided material and the length of suture and maintain the axially compressed state (730). In certain embodiments the binding element may have a thinner portion that extends proximally from the thicker portion and wherein the thinner portion may be disposed within the implant during the steps of threading and pulling; and the thinner portion is pulled proximally to achieve the drawing step. In other embodiments the anchoring implant may be inserted into a prepared bone tunnel prior to the step of pulling and the length of suture may be connected with a piece of soft tissue to be attached to an area adjacent the bone tunnel.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A soft material anchoring system comprising:
   an anchoring implant comprising braided fibers, having an elongate state for inserting into a bone tunnel, and a radially expanded state wherein the anchoring implant is configured to expand into walls of the bone tunnel;
   a suture extending along and through a sidewall of the anchoring implant, wherein the suture is configured to adjust the anchoring implant from the elongate state to the radially expanded state; and
   a binding element at least partially extending within the anchoring implant, the binding element comprising a binding portion and a non-binding portion, the binding portion larger in diameter than the non-binding portion and configured to lock the anchoring implant in the radially expanded state.

2. The soft material anchoring system of claim 1, wherein when the binding portion is disposed within the anchoring implant, the suture is inhibited from sliding.

3. The soft material anchoring system of claim 1, wherein when the binding portion is disposed within the anchoring implant the braided fibers are inhibited from sliding over each other, to lock the anchoring implant in the radially expanded state.

4. The soft material anchoring system of claim 1, wherein the binding element is tapered between the binding portion and the non-binding portion.

5. The soft material anchoring system of claim 1, wherein the binding element s a suture loop that interweaves through at least a portion of the implant sidewall.

6. The soft material anchoring system of claim 1, wherein the binding element extends along a central lumen of the anchoring implant.

7. The soft material anchoring system of claim 1, wherein the binding element is configured to move along the anchoring implant and when the binding portion is externally disposed relative to the anchoring implant the suture may slide through the anchoring implant.

8. The soft material anchoring system of claim 1, wherein tension applied the suture is operable to move the anchoring implant from the elongate state to the expanded state.

9. The soft material anchoring system of claim 1 wherein while in the elongate state, the binding portion is external to the anchoring implant and wherein when locked, the binding portion is at least partially disposed within the anchoring implant.

10. A soft material anchoring system comprising:
an anchoring implant comprising braided fibers, having an elongate state configured for insertion into a bone tunnel, and a radially expanded state for anchoring within the bone tunnel;
at least one suture interwoven through and along a sidewall of the anchoring implant, configured to slide through the anchoring implant and adjust the anchoring implant from the elongate state to the radially expanded state; and
a binding element extending through a lumen of the anchoring implant, the binding element comprising a binding portion and a non-binding portion, wherein the binding portion is configured to move along the lumen and inhibit the at least one suture from sliding.

11. The soft material anchoring system of claim 10 wherein the binding portion is configured to move between a first position and a second position, wherein in the first position the binding portion is external to the anchoring implant and in the second position the binding portion is disposed within the anchoring implant lumen.

12. The soft material anchoring system of claim 10 wherein the binding portion is moveable between a first position and a second position, wherein in the first position the binding portion is substantially external to the anchoring implant and in the second position the binding portion is disposed within the anchoring implant lumen so as to lock the anchoring implant in the radially expanded state.

13. The soft material anchoring system of claim 10, wherein the binding portion defines a thicker portion of a suture structure than the non-binding portion.

14. The soft material anchoring system of claim 10 wherein the binding element is disposed along central lumen of the anchoring implant.

15. A soft material anchoring system comprising:
an anchoring implant comprising, braided suture, having an elongate state wherein the implant is configured to be inserted within a bone tunnel, and a laterally expanded state wherein the anchoring implant is configured to anchor within the bone tunnel;
a first suture interwoven through and along a sidewall of the anchoring implant, configured to adjust the anchoring implant from the elongate state to the laterally expanded state; and
a binding element at least partially extending through and moveable along the anchoring implant, the binding element defining a first portion and a second portion, the first portion thicker than the second portion, the first portion configured to lock the anchoring implant in the laterally expanded state when moved into the anchoring implant.

16. The anchoring system of claim 15, wherein the binding element defines a second suture, distinct from the first suture, and wherein the first portion defines a thicker portion of the second suture than the second portion.

17. The soft material anchoring system of claim 15 wherein the anchoring implant defines a tube having a distal end and a proximal end, with the lumen extending therebetween, and wherein the first portion of the binding element is at least partially drawn towards the proximal end of the tube and into the tube distal end and lumen so as to lock the soft anchoring implant in the laterally expanded state.

18. The soft material anchoring system of claim 15 further comprising a tapered portion of the binding element, defining a transition between the first portion and the second portion, the transition configured to aid in drawing the first portion into the anchoring implant so as to lock the anchoring implant in the laterally expanded state.

* * * * *